United States Patent [19]
Burrows

[11] Patent Number: 6,143,034
[45] Date of Patent: Nov. 7, 2000

[54] IMPLANTABLE HINGED KNEE PROSTHESIS HAVING TIBIAL BASEPLATE

[75] Inventor: James W. Burrows, Cedar Park, Tex.

[73] Assignee: Sulzer Orthopedics Inc., Austin, Tex.

[21] Appl. No.: 09/126,706

[22] Filed: Jul. 30, 1998

[51] Int. Cl.[7] ...................................................... A61F 2/38
[52] U.S. Cl. ............................................................. 623/20
[58] Field of Search ................................... 623/18, 20, 16

[56] References Cited

U.S. PATENT DOCUMENTS

| | | | |
|---|---|---|---|
| 3,813,700 | 6/1974 | Tavernetti et al. | 623/20 |
| 3,824,630 | 7/1974 | Johnston | 623/20 |
| 5,437,287 | 8/1995 | Phillips et al. | 128/898 |
| 5,755,804 | 5/1998 | Schmotzer et al. | 623/20 |

*Primary Examiner*—David J. Isabella
*Attorney, Agent, or Firm*—Philip S. Lyren; Kenneth S. Barrow

[57] ABSTRACT

An implantable orthopedic knee joint prosthesis. A femoral component has a first body including a surface for engaging femoral bone and a second body including a surface for engaging another component. Means are provided for hingedly connecting the first and second bodies together for relative pivoting motion about a fixed pivot axis. A tibial component has a baseplate that includes a surface for engaging tibial bone and a surface for engaging another component. An adapter bearing is disposed intermediate the second body and the baseplate and includes means for engagement with and affixation to the baseplate, and means for engagement with and affixation to the second body. A keel depends from the tibial bone engaging surface of the baseplate.

19 Claims, 2 Drawing Sheets

IMPLANTABLE HINGED KNEE PROSTHESIS HAVING TIBIAL BASEPLATE

BACKGROUND OF THE INVENTION

FIELD OF THE INVENTION

The present invention relates generally to implantable prostheses for replacing human skeletal joints, and relates more particularly to multiple components of an implantable total knee prosthesis for replacing the articulating surfaces of a human knee joint.

BACKGROUND INFORMATION

Implantable orthopedic prostheses, in one form, comprise manufactured replacements for the ends and articulating surfaces of the bones of the skeleton. Such prostheses are implanted to repair or reconstruct all or part of an articulating skeletal joint that is functioning abnormally due to disease, trauma, or congenital defect. Among the various articulating skeletal joints of the human body that are eligible to be fitted with implantable orthopedic prostheses, the knee joint is one of the joints most often treated with such prostheses. The knee joint is a major weight bearing joint and degenerates more quickly than many other joints in case of abnormality. Also, the knee joint plays a critical role in ambulation and quality of life, resulting in great demand for surgical correction of abnormalities.

The human knee joint involves three bones: the femur, the tibia and the patella, each having smooth articulation surfaces arranged for articulation on an adjacent articulation surface of at least one other bone. The femur includes at its distal extremity an articulation surface having medial and lateral convex condyles separated posteriorly by an intercondylar groove running generally in the anterior-posterior direction, the condyles joining at the distal-anterior face of the femur to form a patellar surface having a shallow vertical groove as an extension of the intercondylar groove. The patella includes on its posterior face an articulation surface having a vertical ridge separating medial and lateral convex facets, which facets articulate against the patellar surface of the femur and against the medial and lateral condyles during flexion of the knee joint, while the vertical ridge rides within the intercondylar groove to prevent lateral displacement of the patella during flexion. The tibia includes at its proximal end an articulation surface having medial and lateral meniscal condyles that articulate against the medial and lateral condyles, respectively, of the femur. The mutually engaging articulation surfaces of the femur and the patella together form, functionally, the patellofemoral joint, and the mutually engaging articulation surfaces of the femur and tibia together form, functionally, the tibiofemoral joint, which two functional joints together form the anatomical knee joint.

All or part of one or more of the articulation surfaces of the knee joint may fail to act properly, requiring the defective natural articulation surface to be replaced with a prosthetic articulation surface provided by an implantable prosthesis. To fit defects of varying scope, while allowing healthy portions of the knee joint to be conserved, a range of types of orthopedic knee implants is available. The range extends from total knee prosthesis systems for replacing the entire articulation surface of each of the femur, tibia and patella, to simpler systems for replacing only the tibiofemoral joint, or only one side (medial or lateral) of the tibiofemoral joint, or only the patellofemoral joint. Commonly employed orthopedic knee prostheses include components that fall within one of three principle categories: femoral components, tibial components, and patellar components. A so-called "total" knee prosthesis includes components from each of these categories. The femoral component replaces the distal end and condylar articulating surfaces of the femur and may include a proximal stem received within the medullary canal at the distal end of the femur. The tibial component replaces the proximal end and meniscal articulating surfaces of the tibia and may include a distal stem received within the medullary canal at the proximal end of the tibia. The patellar component replaces the posterior side and natural articulating surface of the patella. Sometimes, the patellar component is not used, and the natural articulating surface of the patella is allowed to articulate against the femoral component. A so-called "unicondylar" knee prosthesis replaces only the medial or the lateral femoral condylar articulating surface and the corresponding tibial meniscal articulating surface. Where soft tissue structures are relatively intact, it is preferred to employ prosthetic articulating surfaces shaped similarly to the natural articulating surfaces to replicate the natural motion of the knee. Where soft tissues are compromised, or the bone where the soft tissue attaches is compromised, the prosthetic articulating surfaces are preferred to be constrained to some degree. In extreme cases, a hinged knee prosthesis is employed in which the femoral component is connected to the tibial component by a hinge connection that constrains the flexion and extension of the knee about a fixed pivot axis.

As used herein, the words proximal and distal are terms of reference that indicate a particular portion of a prosthesis component according to the relative disposition of the portion when the component is implanted. "Proximal" indicates that portion of a component nearest the torso, whereas "distal" indicates that portion of the component farthest from the torso. Directional terms of reference used herein include superior, inferior, anterior, posterior, medial and lateral, which are used according to their commonly understood anatomical meanings. More particularly, with regard to a person in a standing position, superior means upward, inferior means downward, anterior means forward, posterior means rearward, medial means inwardly from the side toward the center of the body, and lateral means outwardly from the center of the body toward the side.

The tibial component of a total knee prosthesis is configured to be received upon and fixed to the proximal end of the tibia. The tibia is prepared to receive the tibial component by resecting part of the proximal end of the tibia to leave a substantially horizontal planar bony plateau. Sometimes the exposed medullary canal at the proximal end of the tibia is also reamed to receive a stem portion of the tibial component. The tibial component typically includes a plate portion having an inferior planar surface conforming to the resected bony plateau at the proximal end of the femur. The plate portion may or may not include a depending stem or keel for receipt within a prepared tibial medullary canal. Commonly, a meniscal bearing insert is received atop the plate portion of the tibial component to provide an artificial meniscal articulating surface for receiving the condylar surfaces of the femoral component of the total hip prosthesis. The femoral condylar articulating surfaces articulate against the tibial meniscal articulating surface to restore motion to a defective knee joint.

One known type of tibial component involves a tibial plate made of a bio-compatible metal such as titanium or a titanium alloy, and a meniscal bearing insert made of a bio-compatible polymer such as ultra-high molecular weight polyethylene. The tibial plate is shaped generally as a flat plate having a perimeter that generally conforms to the transverse sectional perimeter of the resected proximal tibia. The tibial plate includes a planar distal, or inferior, surface for engaging the resected proximal tibia, and a proximal, or superior, surface for engaging and receiving the meniscal bearing insert. One or more screw holes may extend through the plate portion from the superior to the inferior surface. The bearing insert has an inferior surface that engages the superior surface of the plate portion, and may include locking tabs or other means for fixing the bearing insert to the plate portion against relative movement. The tibial plate can be affixed to the resected tibial bone by bone screws or bone cement. If bone screws are elected, the screws are driven into the bone through the screw holes before the bearing insert is placed atop the plate portion. The plate also can be affixed by a combination of bone screws and bone cement.

SUMMARY OF THE INVENTION

According to one aspect of the present invention, an implantable orthopedic knee joint prosthesis includes a femoral component having a first body including a femoral bone engaging surface and a second body including a prosthesis component engaging surface, and means for hingedly connecting the first and second bodies together for relative pivoting motion about a fixed pivot axis. Also included is a tibial component having a baseplate with a tibial bone engaging surface and a prosthesis component engaging surface. An adapter bearing is disposed intermediate the second body of the femoral component and the baseplate of the tibial component. The adapter bearing has means for engagement with and affixation to the baseplate, and has means for engagement with and affixation to the second body of the femoral baseplate.

It is an object of the present invention to provide an improved implantable orthopedic total knee prosthesis providing a hinged femoral component and a bone-conserving tibial component.

Other objects and advantages of the present invention will be apparent from the following descriptions of the preferred embodiments illustrated in the drawings.

DETAILED DESCRIPTION OF THE PREFERED EMBODIMENT

Figure 1:
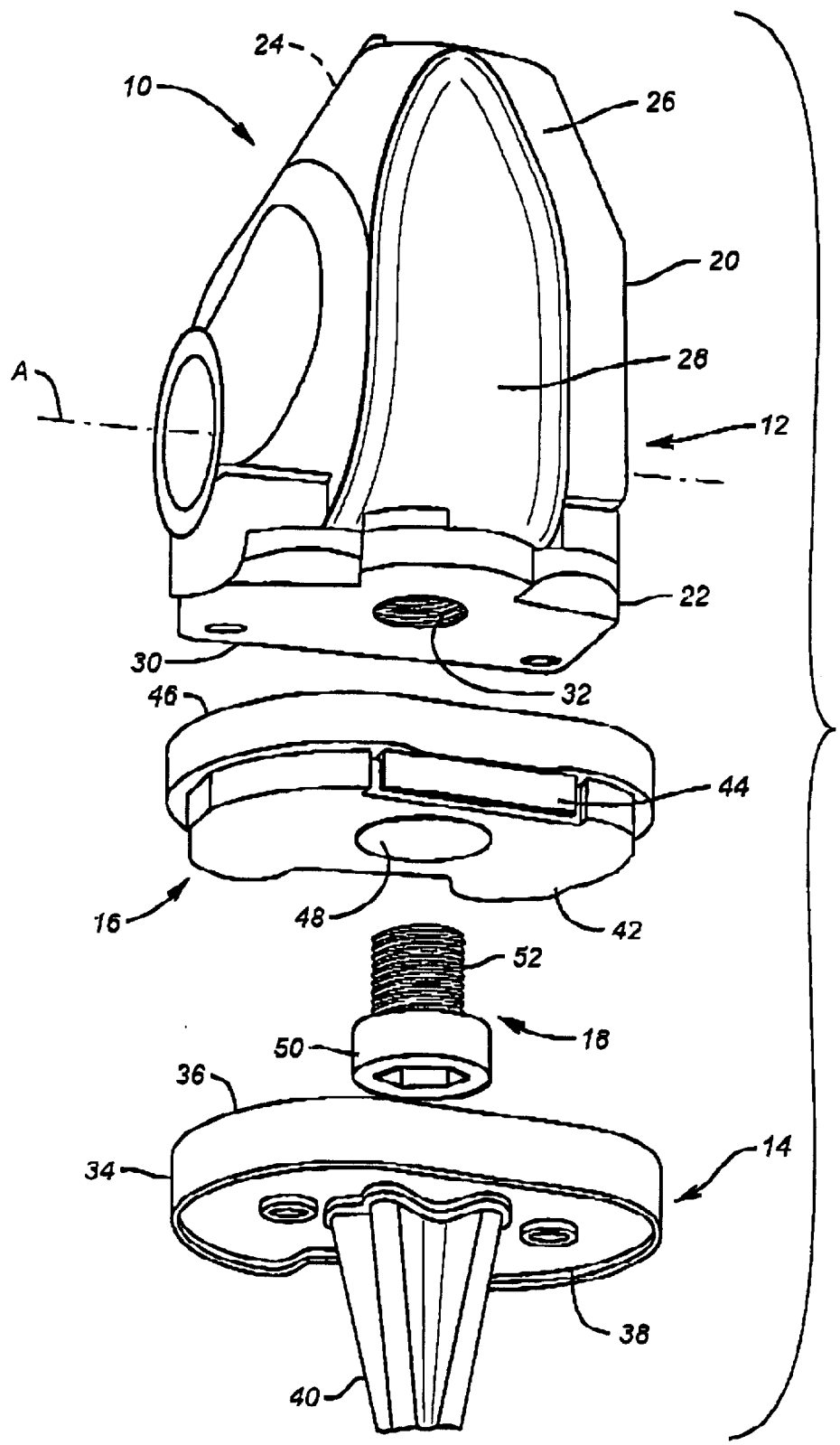
FIG. 1 is an exploded perspective view of a total knee prosthesis according to the present invention.
Figure 2:
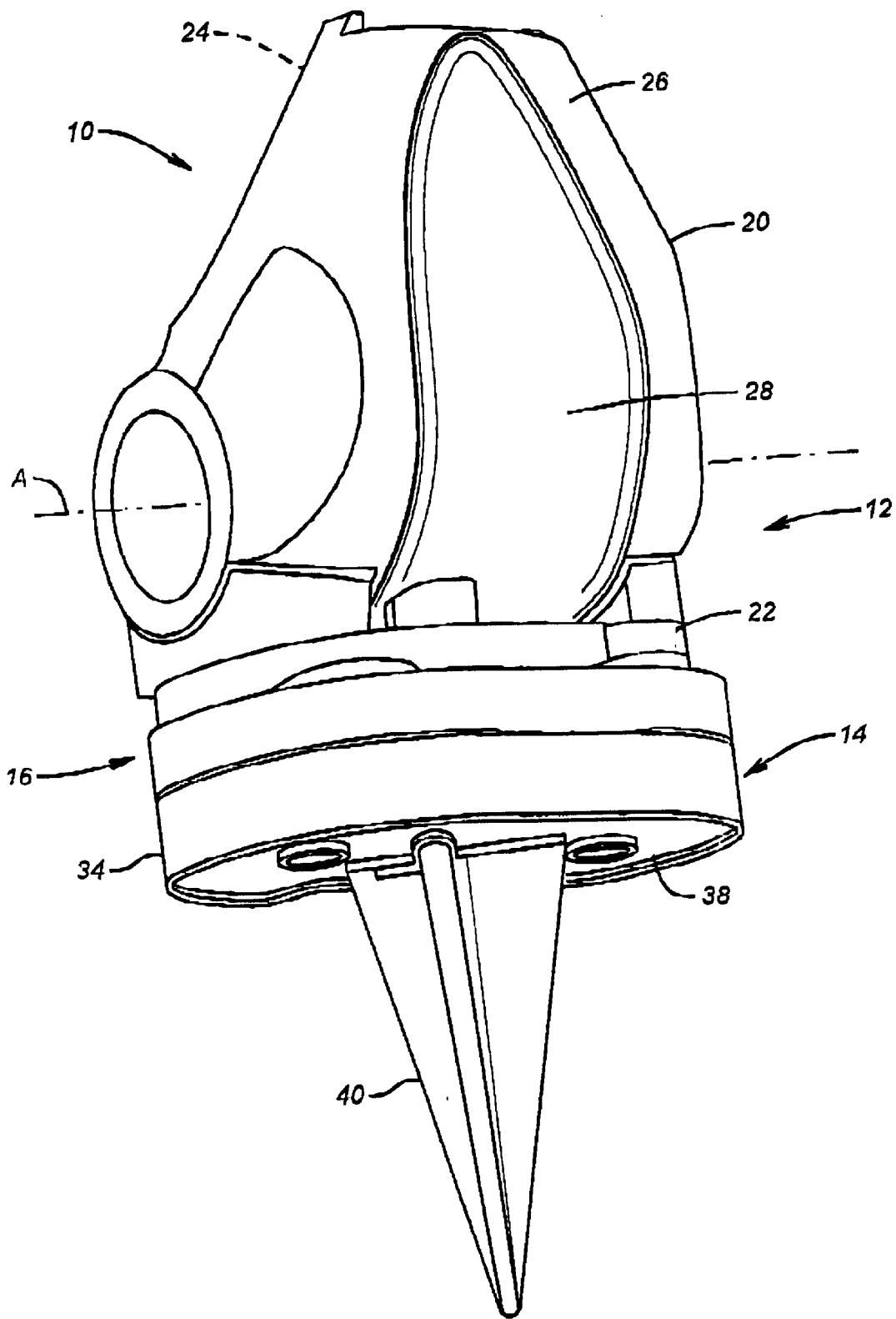
FIG. 2 is an assembled perspective view of the total knee prosthesis of FIG. 1.

Referring to FIGS. 1 and 2, a preferred embodiment of the present invention is illustrated. Total knee prosthesis 10 includes as principle components a femoral component 12, a tibial component 14, an adapter bearing 16, and a bolt 18. Femoral component 12 includes a first body 20 and a second body 22. First body 20 and second body 22 are hinged together such that first body 22 is constrained to pivot relative to second body 22 about a fixed pivot axis A. First body 20 includes a proximal surface 24 having a connecting element such as a taper or the like for connection to an intermediary stem (not shown). The intermediary is inserted within the medullary canal of the femur, and fixes the prosthesis to the distal femur in conventional fashion. An anterior surface 26 of first body 20 includes a shallow patellar groove 28 that is polished to provide a prosthetic articulating surface against which the patella or a patellar prosthesis articulates. Second body 22, in addition to having a hinge structure that cooperates with a hinge structure of first body 20 to constrain relative rotation about pivot axis A, also has a substantially planar inferior surface 30 for interfacing with and engaging another component of the total knee system. Substantially centered in inferior surface 30 is an internally threaded hole 32 having an axis extending in the superior-inferior direction. Femoral component 12, comprising sub-components 20 and 22, is configured in the manner of a hinged femoral component of the type that is used in a modular total knee system for treating bone oncology patients where highly variable amounts of bone may need to be removed to treat the bone cancer.

Tibial component 14 is configured in conventional fashion as a tibial baseplate and keel of the type that is used with an ultra high molecular weight polyethylene bearing insert in a non-constrained primary total knee prosthesis. The combination of a conventional primary tibial component 14 and a hinged femoral component 12 of a modular oncology knee prosthesis system provides special advantages for some patients. Typical prior hinged knee systems involve a long stem on the tibial component for insertion within the tibial medullary canal. In contrast, the relatively short keel of a primary tibial baseplate requires substantially less tibial bone removal during implantation. This is especially advantageous for young oncology patients because there is less disruption of the tibial growth plate. The present combination of femoral and tibial components also permits a conventional primary knee prosthesis to be converted to a hinged knee prosthesis, should deterioration of knee stability so warrant, without disturbing the primary tibial component. Tibial component 14 includes a baseplate 34 having a superior, generally planar surface 36 configured for receiving and engaging a UHMW polyethylene bearing insert, and an inferior, generally planar surface 38 for engaging and affixation to a resected bony plateau of the proximal tibia. A tibial keel 40 depends from inferior surface 38 of baseplate 34. Keel 40 is generally cruciform in cross-section and tapers inferiorly and inwardly.

Adapter bearing 16, disposed between femoral component 12 and tibial component 14, is configured to adapt each of femoral component 12 and tibial component 14 for connection to each other. Adapter bearing 16 is constructed of ultra high molecular weight polyethylene in the manner of a conventional tibial bearing insert of a primary knee prosthesis system. Like such a conventional polyethylene tibial bearing insert, adapter bearing 16 includes a substantially planar inferior surface 42 for engaging superior planar surface 36 of baseplate 34. Likewise, adapter bearing 16 includes anterior and posterior locking tabs 44 that interconnect with respective anterior and posterior locking slots in baseplate 34 to secure adapter bearing 16 to baseplate 34 in the same manner in which a conventional bearing insert is secured to a primary tibial baseplate. Adapter bearing 16 differs from a conventional bearing insert by having a substantially planar superior surface 46 for engaging inferior planar surface 30 of second body 22, rather than having a superior surface configured as concave meniscal surfaces for articulating against the convex condyles of a conventional primary femoral component. Adapter bearing 16 also differs from a conventional bearing insert by including a substantially centered through hole 48 extending from the superior surface 46 to the inferior surface 42.

Bolt 18, having a head 50 and a threaded shank 52, is received within through hole 48 from below, such that head 50 is recessed within through hole 48 so that bolt 18 does not protrude inferiorly of inferior surface 42 of adapter bearing 16. Through hole 48 includes an internal shoulder, not shown, by which the diameter of the superior portion of through hole 48 is reduced relative to that of the inferior portion of through hole 48. Head 50 seats against the internal shoulder of through hole 48, whereas the threaded shank 52 of bolt 18 extends therethrough superiorly of superior surface 46 to threadably engage and be received in internally threaded hole 32 of second body 22. When threadably engaged within hole 32, bolt 18 secures adapter bearing 16 to body 22 of femoral component 22.

It should be appreciated that when the femoral component 12 and the adapter bearing 16 are secured together by bolt 18, components 12, 16 and 18 are transformed into an integral unit having an interface that snaps into engagement with tibial component 14. This allows a tibial component of a primary knee prosthesis system to be mated to a hinged femoral component of a modular oncology knee prosthesis system, providing benefits for particular classes of patients, including oncology patients in whom it is desirable to interfere minimally with the tibia, and patients already having a primary knee prosthesis whose condition has progressed to the point where a hinged knee is indicated.

The present invention has been illustrated and described with particularity in terms of preferred embodiments. Nevertheless, it should be understood that no limitation of the scope of the invention is intended. The scope of the invention is defined by the claims appended hereto. It should also be understood that variations of the particular embodiments described herein incorporating the principles of the present invention will occur to those of ordinary skill in the art and yet be within the scope of the appended claims.

I claim:

1. An implantable orthopedic knee joint prosthesis comprising
    a femoral component having a first body and a second body having a base plate including a prosthesis component engaging surface, and means for hingedly connecting said first and second bodies together for relative pivoting motion about a fixed pivot axis;
    a tibial component having a baseplate including a tibial bone engaging surface and a prosthesis component engaging surface;
    an adapter bearing disposed intermediate said second body of said femoral component and said baseplate of said tibial component, said adapter bearing having means for engagement with and affixation to said baseplate, and having means for engagement with and affixation to said second body of said femoral baseplate.

2. The implantable orthopedic knee joint prosthesis of claim 1, in which said tibial component includes a keel depending from said tibial bone engaging surface.

3. The implantable orthopedic knee joint prosthesis of claim 2, in which said keel is substantially cruciform in cross-section.

4. The implantable orthopedic knee joint prosthesis of claim 1, in which said means of said adapter bearing for engagement with and affixation to said baseplate includes tabs on said adapter bearing in snap engagement with slots in said baseplate.

5. The implantable orthopedic knee joint prosthesis of claim 1, in which said means of said adapter bearing for engagement with and affixation to said second body of said femoral baseplate includes a bolt received through said adapter bearing an connected to said second body.

6. The implantable orthopedic knee joint prosthesis of claim 1, in which said adapter bearing includes a superior surface in engagement with said component engaging surface of said second body of said femoral component.

7. The implantable orthopedic knee joint prosthesis of claim 6, in which said means of said adapter bearing for engagement with and affixation to said baseplate includes tabs on said adapter bearing in snap engagement with slots in said baseplate.

8. The implantable orthopedic knee joint prosthesis of claim 7, in which said means of said adapter bearing for engagement with and affixation to said second body of said femoral baseplate includes a bolt received through said adapter bearing an connected to said second body.

9. The implantable orthopedic knee joint prosthesis of claim 1, in which said adapter bearing includes an inferior surface in engagement with said component engaging surface of said baseplate of said tibial component.

10. The implantable orthopedic knee joint prosthesis of claim 9, in which said means of said adapter bearing for engagement with and affixation to said baseplate includes tabs on said adapter bearing in snap engagement with slots in said baseplate.

11. The implantable orthopedic knee joint prosthesis of claim 10, in which said means of said adapter bearing for engagement with and affixation to said second body of said femoral baseplate includes a bolt received through said adapter bearing an connected to said second body.

12. The implantable orthopedic knee joint prosthesis of claim 10, in which said tibial component includes a keel depending from said tibial bone engaging surface.

13. The implantable orthopedic knee joint prosthesis of claim 12, in which said keel is substantially cruciform in cross-section.

14. The implantable orthopedic knee joint prosthesis of claim 10, in which said keel is substantially cruciform in cross-section.

15. An implantable orthopedic knee joint prosthesis comprising
    a femoral component having a first body and a second body including a prosthesis component engaging surface, said first body being pivotally connected to said second body;
    a tibial component having a baseplate including a tibial bone engaging surface for engaging a tibial bone, and a prosthesis component engaging surface;
    an adapter bearing having a first surface and a second surface, said adapter bearing being disposed intermediate said second body of said femoral component and said baseplate of said tibial component and being fixedly secured to said baseplate of said tibial component so that said first surface of said adapter bearing engages with said prosthesis component engaging surface of said tibial component, said adapter bearing being further fixedly secured to second body of said femoral component so that said second surface engages said prosthesis component engaging surface of said second body.

16. The implantable orthopedic knee joint prosthesis of claim 15, in which said tibial component further includes a keel depending from said tibial bone engaging surface.

17. The implantable orthopedic knee joint prosthesis of claim 15, said adapter bearing further comprising at least one tab, and said baseplate of said tibial component further comprising at least one slot corresponding to said at least one tab, said adapter bearing being fixedly secured to said baseplate by snap engagement of said tabs with said slots.

18. The implantable orthopedic knee joint prosthesis of claim 15, wherein said adapter bearing and said baseplate of said femoral component each include a hole therethrough, said adapter plate being fixedly secured to said baseplate by bolt extending through said holes in said adapter bearing and said baseplate.

19. The implantable orthopedic knee joint prosthesis of claim 15, in which said tibial component includes a keel depending from said tibial bone engaging surface.

* * * * *